United States Patent
Suzuki

(10) Patent No.: US 11,786,305 B2
(45) Date of Patent: Oct. 17, 2023

(54) LIGHT TREATMENT SYSTEM AND LIGHT TREATMENT METHOD

(71) Applicant: OLYMPUS CORPORATION, Tokyo (JP)

(72) Inventor: Toshiaki Suzuki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 223 days.

(21) Appl. No.: 17/182,304

(22) Filed: Feb. 23, 2021

(65) Prior Publication Data

US 2021/0196380 A1    Jul. 1, 2021

Related U.S. Application Data

(63) Continuation of application No. PCT/JP2018/040613, filed on Oct. 31, 2018.

(51) Int. Cl.
*A61B 18/20* (2006.01)
*A61B 18/24* (2006.01)
(Continued)

(52) U.S. Cl.
CPC .... *A61B 18/24* (2013.01); *A61B 2018/00517* (2013.01); *A61B 2018/206* (2013.01); *A61B 2018/2261* (2013.01)

(58) Field of Classification Search
CPC .................................. A61B 18/20; A61N 5/06
See application file for complete search history.

(56) References Cited

U.S. PATENT DOCUMENTS

| | | | |
|---|---|---|---|
| 4,612,938 A | | 9/1986 | Dietrich et al. |
| 5,303,324 A | * | 4/1994 | Lundahl ............... A61N 5/0601 606/7 |

(Continued)

FOREIGN PATENT DOCUMENTS

| | | |
|---|---|---|
| EP | 04411132 A1 | 2/1991 |
| JP | S59-95065 A | 5/1984 |

(Continued)

OTHER PUBLICATIONS

International Search Report dated Jan. 22, 2019 issued in PCT/JP2018/040613.

(Continued)

*Primary Examiner* — Lynsey C Eiseman
(74) *Attorney, Agent, or Firm* — Scully, Scott, Murphy & Presser, P.C.

(57) ABSTRACT

A light treatment system includes: a probe configured to be inserted into a bladder, the probe including an optical fiber, and a diffuser that is provided at a distal end of the optical fiber, the diffuser being configured to emit the light from a surface of the cylindrical shape in a diffused manner; a balloon catheter into which the probe is inserted, the balloon catheter being configured to be inserted into the bladder, the balloon catheter including a distal end portion that is to be spherically dilated in the bladder; and a liquid that includes light scattering particles and fills inside of the distal end portion when the distal end portion has been dilated, the liquid having an equivalent scattering coefficient $\mu'_s$ equal to or larger than 5/R, where R is a maximum radius of the distal end portion that has been dilated.

6 Claims, 7 Drawing Sheets

(51) Int. Cl.
  *A61B 18/00* (2006.01)
  *A61B 18/22* (2006.01)

(56) References Cited

U.S. PATENT DOCUMENTS

| | | | |
|---|---|---|---|
| 2004/0039242 A1 | 2/2004 | Tolkoff et al. | |
| 2006/0104593 A1* | 5/2006 | Gowda | A61N 5/062 |
| | | | 385/139 |
| 2006/0253178 A1* | 11/2006 | Masotti | A61N 5/0601 |
| | | | 606/13 |
| 2016/0151639 A1* | 6/2016 | Scharf | A61N 5/0624 |
| | | | 607/92 |
| 2018/0311508 A1* | 11/2018 | Ellingwood | A61M 25/00 |

FOREIGN PATENT DOCUMENTS

| | | |
|---|---|---|
| JP | H2-98373 A | 4/1990 |
| JP | 2005-531336 A | 10/2005 |
| WO | WO 03/084601 A2 | 10/2003 |

OTHER PUBLICATIONS

Uchibayashi, T., et al., "An Experimentalstudy of Whole Bladder Wallphotodynamic Therapy Using Alight-Scattering Medium", The Japanese Journal of Urology (May 1988), vol. 79, No. 5, pp. 807-813, with English abstract and partial translation, cited in spec on p. 2.

Misaki, T. et al., "Photodynamictherapy for Superficial Bladdertumors", Acta Urologica Japonica (Dec. 1986), vol. 32, No. 12, pp. 1941-1948, cited in spec on p. 3, with English abstract.

* cited by examiner

LIGHT TREATMENT SYSTEM AND LIGHT TREATMENT METHOD

CROSS-REFERENCE TO RELATED APPLICATION

This application is a continuation of International Application No. PCT/JP2018/040613, filed on Oct. 31, 2018, the entire contents of which are incorporated herein by reference.

BACKGROUND

1. Technical Field

The present disclosure relates to light treatment systems and light treatment methods.

2. Related Art

Light treatment systems for performing treatment using light have been known (see, for example, Japanese Patent Application Laid-open No. S59-095065). In these light treatment systems, a sac-like balloon is attached to a distal end of a tubular catheter to be inserted into a hollow organ of a human body, such as the bladder. A light conductor, such as optical fiber, is inserted in the catheter and a diffuser at a distal end of the light conductor is placed in the balloon. The diffuser emits treatment light forward. The balloon is filled with a scattering medium including fat emulsion diluted with a physiological saline solution. Therefore, the treatment light is scattered, and not only the upper part of the bladder, but also the lower part of the bladder is illuminated with the treatment light.

Intralipos at an adjusted concentration of 0.5%, which is one of specific examples of the fat emulsion included in the scattering medium, has been disclosed, for example (see an article, hereinafter referred to as Non-Patent Literature 1, and titled, "Experimental Research on Whole Bladder Wall Photodynamic Therapy Using Scattering Medium", by Tadao Uchibayashi, et al., in Japanese Journal of Urology, May 1988, Vol. 79, No. 5, at pp. 807-813, for example). According to the experimental results described in Non-Patent Literature 1, by filling a bladder with 200 ml of an aqueous solution of Intralipos at a concentration of 0.5%, the bladder is able to be assumed to be a sphere having a radius of 3.6 cm (200 [ml]≈(4π/3)×3.6³ [cm³])). In this case, when laser light of power of 500 mW is emitted from the distal end of the optical fiber and the inner wall of the bladder is evenly illuminated with the laser light, the light power per unit area is calculated to be 500 [mW]/(4π×3.6² [cm²])≈3 [mW/cm²] assuming no light absorption by the scattering medium. However, this article describes that the power of light that the surface of the bladder is irradiated with is about 1.4 mW/cm². This light power is just 0.28% of the power of the emitted laser light. This is because fat emulsion has the property of absorbing light. That is, it is understood that when a bladder is irradiated with laser light in a state where the balloon has been filled with a scattering medium including fat emulsion, the fat emulsion absorbs the laser light, and the power of the laser light is thus significantly attenuated before the laser light reaches the inner wall of the bladder.

Furthermore, according to an article titled, "Photodynamic Laser Treatment of Bladder Tumors", by Toshimitsu Misaki, et al., in Acta Urologica Japonica, December 1986, Vol. 32, No. 12, at pp. 1941-1948, irradiation energy of 100 J/cm² is needed for laser light to achieve laser treatment effects on a tumor in a bladder. Assuming that the surface of the bladder is irradiated with light having power of 1.4 mW/cm², from the results in Non-Patent Literature 1, to obtain the irradiation energy mentioned above, light irradiation as long as about 2 hours (≈100 [J/cm²]÷1.4 [mW/cm²]) is needed and such long light irradiation puts a large burden on the patient. To alleviate the burden on the patient, using high power laser light in the order of watts may be considered, but the use of high power laser light causes problems, such as thermal damage of the optical fiber and increase in size of the light source device.

SUMMARY

In some embodiments, a light treatment system includes: a probe configured to be inserted into a bladder, the probe including an optical fiber configured to propagate light, and a diffuser that is provided at a distal end of the optical fiber and has a cylindrical shape, the diffuser being configured to emit the light from a surface of the cylindrical shape in a diffused manner; a balloon catheter into which the probe is inserted, the balloon catheter being configured to be inserted into the bladder, the balloon catheter including a distal end portion that is to be spherically dilated in the bladder; and a liquid that includes light scattering particles and fills inside of the distal end portion when the distal end portion has been dilated, the liquid having an equivalent scattering coefficient $\mu'_s$ equal to or larger than 5/R, where R is a maximum radius of the distal end portion that has been dilated.

In some embodiments, a light treatment system includes: a probe configured to be inserted into a bladder, the probe including an optical fiber configured to propagate light, and a diffuser that is provided at a distal end of the optical fiber and has a cylindrical shape, the diffuser being configured to emit the light from a surface of the cylindrical shape in a diffused manner; a balloon catheter into which the probe is inserted, the balloon catheter being configured to be inserted into the bladder, the balloon catheter including a distal end portion that is to be spherically dilated in the bladder; and a liquid that includes light scattering particles and fills inside of the distal end portion when the distal end portion has been dilated, the liquid having an equivalent scattering coefficient $\mu'_s$ equal to or larger than $1/7$ [mm$^{-1}$].

In some embodiments, a light treatment method includes: inserting a balloon catheter and a probe into a bladder, the balloon catheter including a distal end portion that is spherically dilatable, the probe being configured to be inserted into the balloon catheter, the probe including a cylindrical distal end portion configured to emit light for treatment in a diffused manner; fixing the distal end portion of the balloon catheter in the bladder by supplying a liquid including light scattering particles to the distal end portion of the balloon catheter to dilate the distal end portion of the balloon catheter, the liquid having an equivalent scattering coefficient $\mu'_s$ equal to or larger than 5/R, where R is a maximum radius of the distal end portion of the balloon catheter that has been dilated; and irradiating inside of the bladder with the light from the probe.

In some embodiments, a light treatment method includes: inserting a balloon catheter and a probe into a bladder, the balloon catheter including a distal end portion that is spherically dilatable, the probe being configured to be inserted into the balloon catheter, the probe including a distal end portion configured to emit light for treatment in a diffused manner and is cylindrical; fixing the distal end portion of the balloon catheter in the bladder by supplying a liquid including light scattering particles to the distal end portion of the balloon catheter to dilate the distal end portion of the balloon catheter, the liquid having an equivalent scattering coefficient $\mu'_s$ equal to or larger than $\frac{1}{7}$ [mm$^{-1}$]; and irradiating inside of the bladder with the light from the probe.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for implementing the disclosure (hereinafter, referred to as "embodiments") will be described below by reference to the appended drawings.

Figure 1:
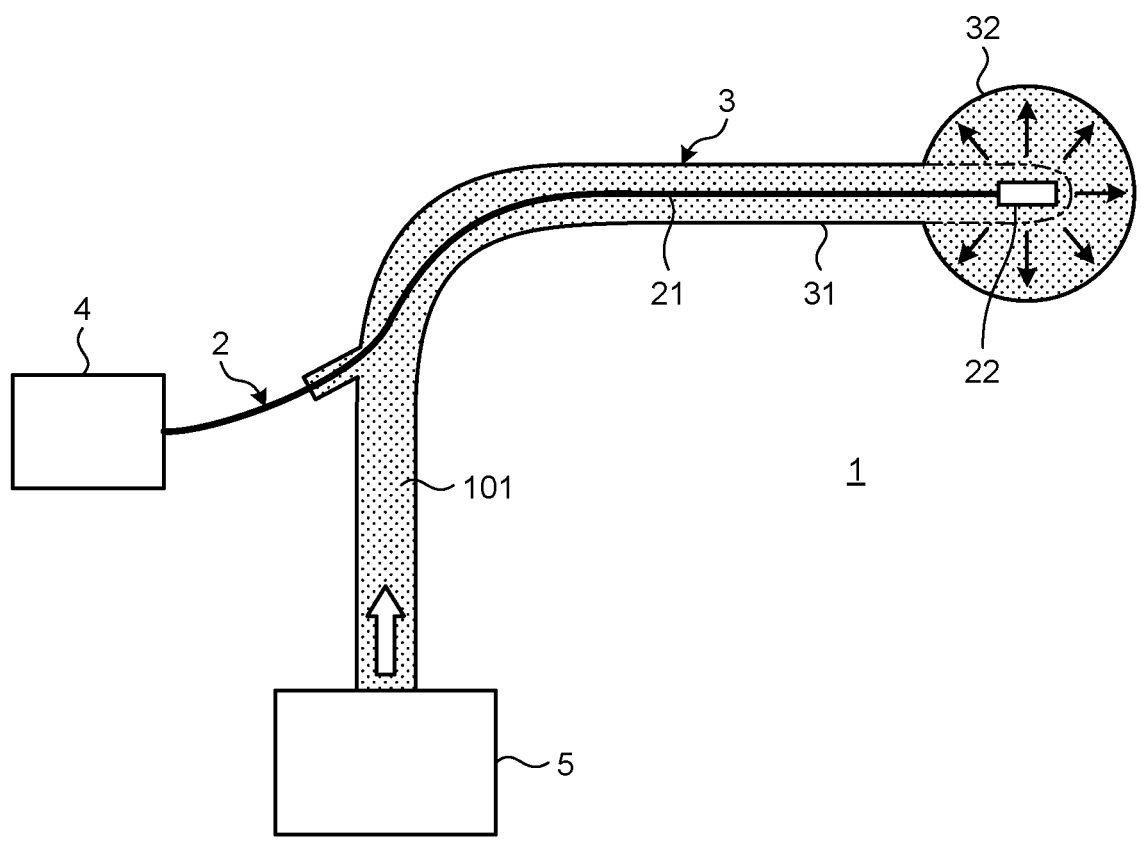
FIG. 1 is a diagram illustrating a configuration of main parts of a light treatment system according to an embodiment.

FIG. 1 is a diagram illustrating a configuration of main parts of a light treatment system according to an embodiment. A light treatment system 1 illustrated in FIG. 1 is a system for treating a bladder by using light. The light treatment system 1 includes a probe 2, a balloon catheter 3, a light source device 4, and a liquid supplying device 5.

Figure 2:
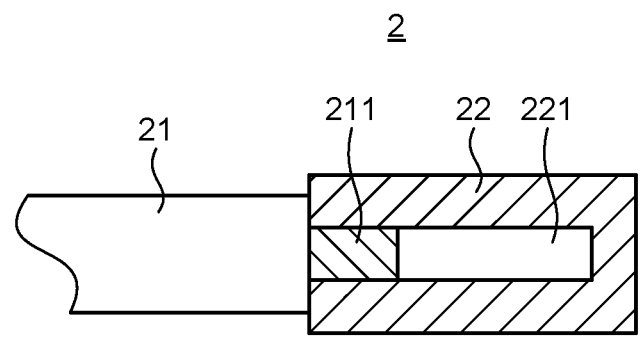
FIG. 2 is a diagram schematically illustrating a configuration of a diffuser.

The probe 2 includes: an optical fiber 21 that propagates light for treatment; and a diffuser 22 that is provided at a distal end of the optical fiber 21, emits laser light propagated through the optical fiber 21 in a diffused manner, and is cylindrical. FIG. 2 is a diagram schematically illustrating a configuration of the diffuser 22. The diffuser 22 has a hollow cylindrical shape with a closed distal end. A distal end of a core 211 of the optical fiber 21 protrudes into an opening at a proximal end of a hollow portion 221 formed in the diffuser 22. The core 211 propagates laser light for treatment and emits the laser light from the distal end of the core 211. The cylindrical shape of the diffuser 22 facilitates insertion of the diffuser 22 into the balloon catheter 3, and as compared with a spherical diffuser, the cylindrical diffuser 22 is able to radiate thermal energy of laser light more efficiently.

The diffuser 22 has a porous structure having quartz beads that have a diameter of 10 μm and have aggregated in close contact with each other. Quartz is a transparent material and scarcely absorbs light. Therefore, laser light incident on the diffuser 22 is repeatedly refracted by innumerable quarts beads inside the diffuser 22 and is emitted as isotropic scattered light from a surface of the diffuser 22.

The aggregate of the quartz beads has a thickness of about 0.7 mm. This aggregate has a property of transmitting about 20% and reflecting about 80%, of incident light in air. Therefore, if the distal end of the optical fiber 21 is in close contact with the aggregate of the quartz beads, most of incident light is reflected towards the optical fiber 21 and is unable to be emitted outside. The diffuser 22 includes the hollow portion 221 formed therein to avoid this situation. Since the hollow portion 221 is formed therein, in liquid, the liquid also enters the hollow portion 221 by permeation of the liquid through the aggregate and reflectance of incident light is thus reduced. Furthermore, most of laser light reflected by an inner wall of the diffuser 22 repeats being reflected by the inner wall or being refracted by the aggregate without returning to the optical fiber 21 and is then emitted outside the diffuser 22.

Figure 3:
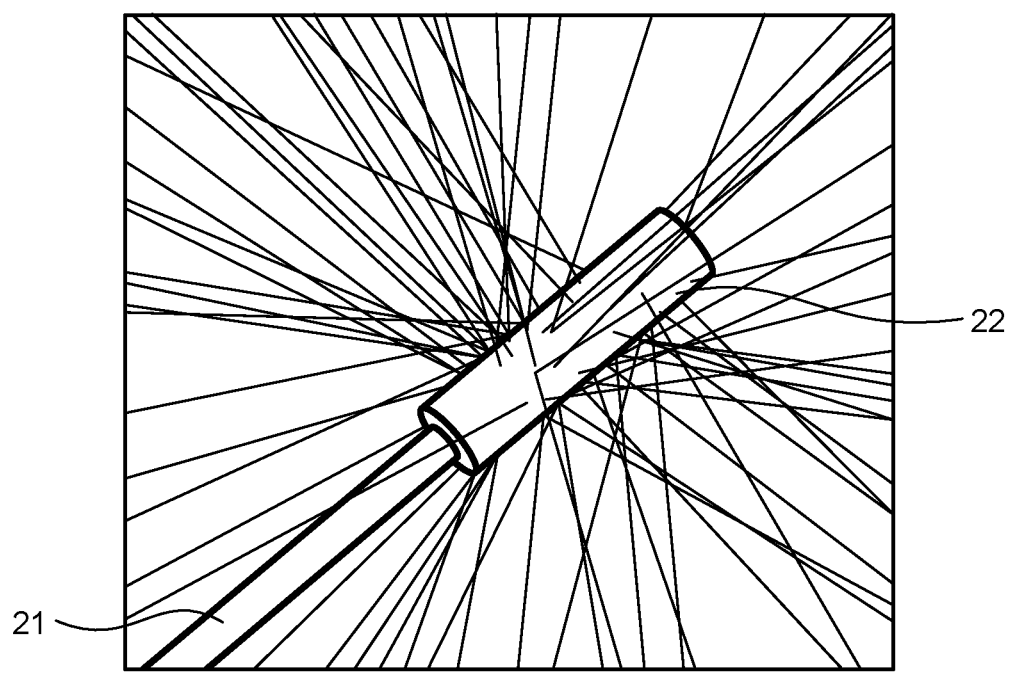
FIG. 3 is a diagram illustrating how light beams emitted by the diffuser are diffused in air.

FIG. 3 is a diagram illustrating how light beams emitted by the diffuser 22 are diffused in air, and is a diagram illustrating results of simulation for tracking the light beams. The diffuser 22 emits treatment light beams in a diffused manner from its cylindrical surface also. Therefore, laser light having emission angles of 90° or more to the left and right is able to be emitted forward along the central axis in the height direction of the cylinder, and a wider range of the inner wall of a bladder is able to be illuminated.

Figure 4:
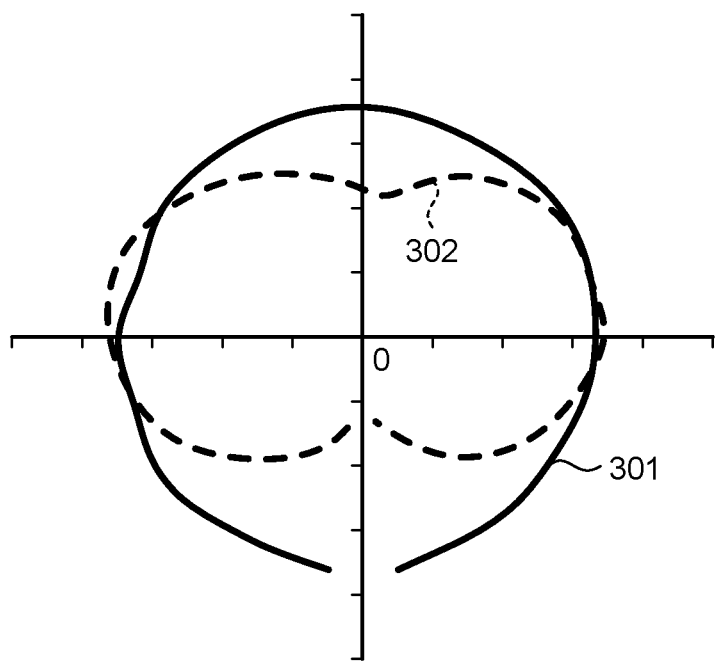
FIG. 4 is a diagram illustrating light distributions of light that is diffused as illustrated in FIG. 3, the light distributions being for radial direction and azimuth direction.
Figure 5:
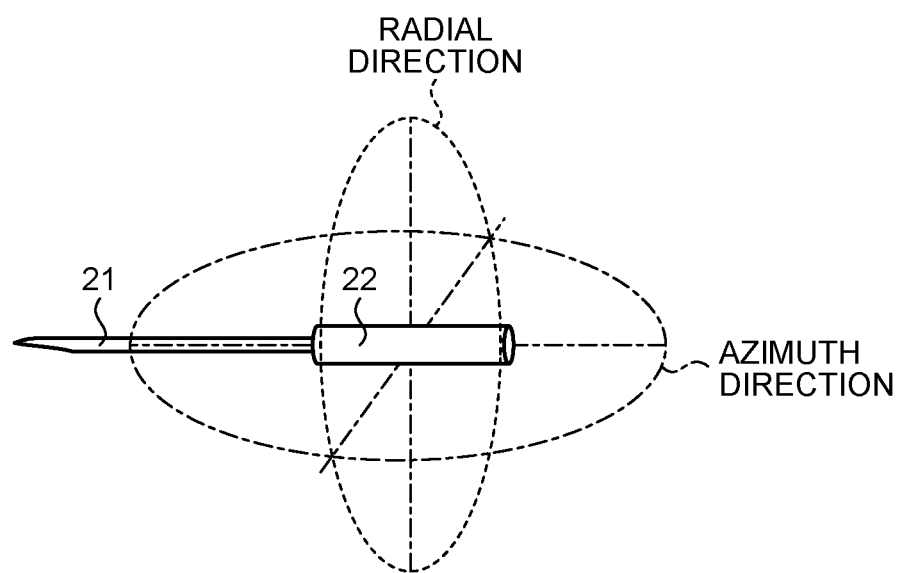
FIG. 5 is a diagram for explanation of the radial direction and azimuth direction.

However, although light emitted by the diffuser 22 is spread in a diffused manner, because the area of the lateral surface of the diffuser 22 is larger than the area of the distal end of the diffuser 22, the light tends to be dark forward and bright laterally. FIG. 4 is a diagram illustrating this situation and is a diagram illustrating superimposed light distributions for radial direction and azimuth direction of light emitted by the diffuser 22. In FIG. 4, a curve 301 represents the distribution for the radial direction and a curve 302 represents the distribution for the azimuth direction. FIG. 5 is a diagram for explanation of the radial direction and azimuth direction. As illustrated in FIG. 5, the radial direction is the direction in which a normal line of the cylindrical surface of the diffuser 22 extends radially, and the azimuth direction is the direction extending in a plane passing the longitudinal central axis of the diffuser 22. The vertical direction in FIG. 4 corresponds to the vertical direction for the radial direction and the front-back direction for the azimuth direction that are illustrated in FIG. 5. The distal end of the diffuser 22 will be referred to as the front and the end connected to the optical fiber 21 will be referred to as the back, herein.

As evident from FIG. 4 also, while the diffusion is approximately isotropic for the radial direction (the curve 301), the diffusion in the front-back direction is smaller than the diffusion in the left-right direction for the azimuth direction (the curve 302). Accordingly, light emitted by the cylindrical diffuser 22 illuminates a wide range in a sphere, but as to the brightness of the illumination, light distribution is uneven for, in particular, the azimuth direction. In this embodiment, supplying a liquid 101 including light scattering particles to a distal end portion 32 of the balloon catheter 3 to adjust concentration as described later randomizes traveling directions of light beams emitted by the diffuser 22 and enables uniform illumination.

The balloon catheter 3 includes: a main body 31 through which the probe 2 is able to be inserted; and the distal end portion 32 that is provided at a distal end of the main body 31 and is spherically dilatable in a bladder. By the distal end portion 32 reaching a bladder and being dilated therein, position of the distal end portion 32 inside the bladder is fixed. The diffuser 22 of the probe 2 reaches the inside of the distal end portion 32, and by the distal end portion 32 being fixed in the bladder, position of the probe 2 in the bladder is fixed. The balloon catheter 3 is made of a material that is thin, elastic, and transparent. This material may be, for example, natural rubber, silicone rubber, or thermoplastic elastomer.

The balloon catheter 3 is filled with the liquid 101 including the light scattering particles, the liquid 101 being supplied by the liquid supplying device 5. The light scattering particles are preferably made of a material that: is comparatively low in light absorptivity, has specific gravity similar to that of water, and has a refractive index different from that of water by a difference larger than a predetermined standard. Examples of the material include plastic microbeads. A solvent that is an aqueous solution of a surfactant or an aqueous solution of glycerol may be used, the aqueous solution having water as the main constituent. When the solvent is an aqueous solution of a surfactant, aggregation of the light scattering particles is able to be prevented. Furthermore, if the solvent is an aqueous solution of glycerol, sedimentation velocity of the light scattering particles is able to be decreased by increase in viscosity of the liquid.

The light source device 4 generates laser light to be supplied to the optical fiber 21. Light generated by the light source device 4 is not limited to laser light.

The liquid supplying device 5 dilates the distal end portion 32 by sending the liquid 101 at a predetermined flow rate or pressure, into the balloon catheter 3.

Figure 6:
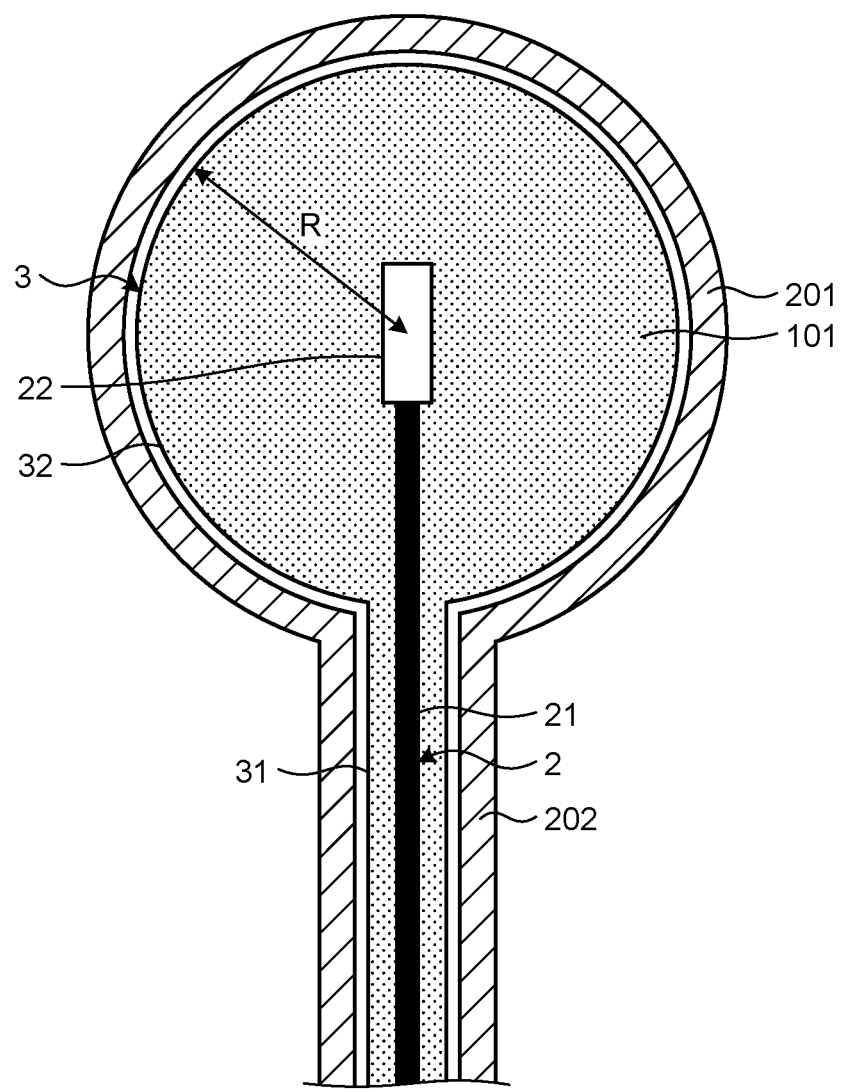
FIG. 6 is a diagram illustrating a state where light treatment is being performed by insertion of the light treatment system according to the embodiment in a bladder.

FIG. 6 is a diagram illustrating a state where light treatment is being performed by insertion of the light treatment system 1 having the above configuration into a bladder 201. When treatment is performed in the state illustrated in FIG. 6, the balloon catheter 3 is inserted into the bladder 201 through a urethra 202, the probe 2 is thereafter inserted into the balloon catheter 3, the liquid 101 is supplied to the distal end portion 32 of the balloon catheter 3, and the distal end portion 32 is thereby spherically dilated and fixed in the bladder 201. Thereafter, the power of the light source device 4 is turned on to cause the light source device 4 to generate laser light for treatment. The diffuser 22 of the probe 2 irradiates inside of the bladder 201 with the laser light generated by the light source device 4 and propagated through the optical fiber 21.

Figure 7:
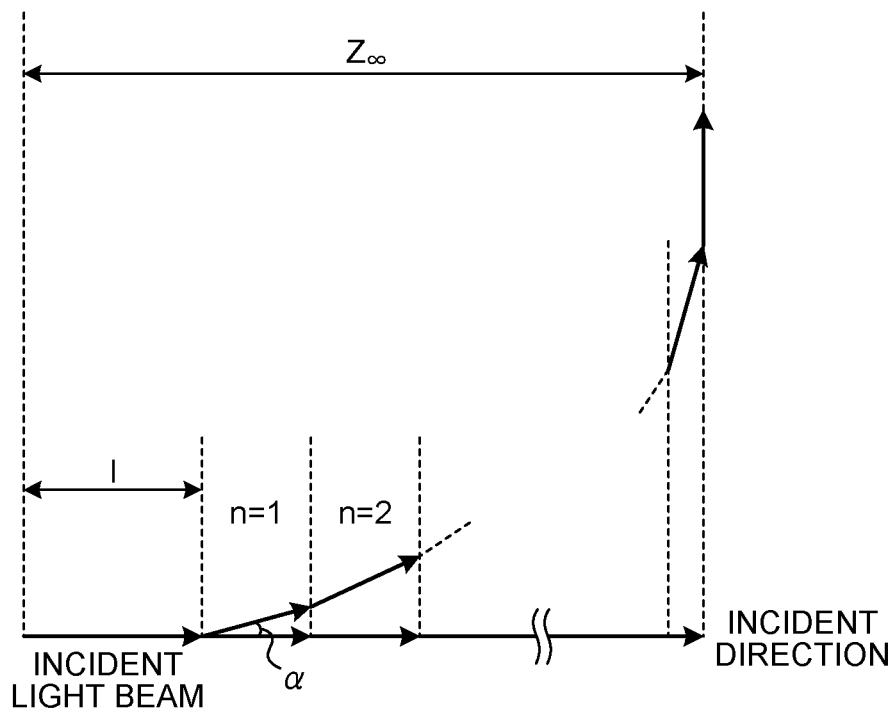
FIG. 7 is a diagram illustrating a model of a process in which traveling directions of light beams become random in multiple scattering of light.

A method of setting a concentration of the light scattering particles will be described below. FIG. 7 is a diagram illustrating a model of a process in which traveling directions of light beams become random in multiple scattering of light. The model illustrated in FIG. 7 represents a situation where a light beam traveling straight collides with a light scattering particle and is scattered at a scattering angle $\alpha$. Because the scattering angle differs every time the light beam is scattered, by using the mean value $<\cos \alpha>$ of projection components of the scattering angles $\alpha$ in the incident direction, a projection component in the incident direction after scattering has been repeated n times is able to be expressed by $<\cos \alpha>^n$. Therefore, the total distance travelled straight $Z_n$ in the incident direction through the scattering of n times is expressed as follows by using the mean distance (the mean free path) l travelled in scattering of one time and the mean value of the projection components $<\cos \alpha>$.

$$Z_n = l(1 + <\cos \alpha> + <\cos \alpha>^2 + \ldots + <\cos \alpha>^n) \quad (1)$$

The mean value $<\cos \alpha>$ of the projection components is called an anisotropic parameter in the Mie scattering theory.

From Equation (1), the total distance travelled straight $Z_\infty$ at the limit of the number of scattering events (n→∞) is expressed as follows.

$$Z_\infty = l/(1 - <\cos \alpha>) \quad (2)$$

This total distance travelled straight $Z_\infty$ will hereinafter be referred to as the transport mean free path. Furthermore, the inverse number $1/Z_\infty$ of the transport mean free path $Z_\infty$ will be referred to as the equivalent scattering coefficient and denoted by $\mu'_s$.

The mean free path and anisotropic parameter are able to be calculated based on the Mie scattering theory if the refractive index of the medium, the diameter of the particles, the refractive index of the particles, and the concentration of the particles are known. Therefore, the transport mean free path $Z_\infty$ and the equivalent scattering coefficient $\mu'_s$ are also able to be calculated. In this embodiment, a liquid having desired light scattering properties is thereby able to be designed and manufactured.

The initial direction component of each light beam emitted toward the inner wall of a bladder from the diffuser 22 is lost and the light beam's traveling direction becomes random, when the light beam has travelled a linear distance worth the transport mean free path $Z_\infty$. The diffuser 22 is placed in the center of the distal end portion 32 and thus to illuminate the inner wall of the bladder with even brightness, at least the maximum radius R (see FIG. 6) of the distal end portion 32 is preferably equal to the transport mean free path $Z_\infty$ or larger.

Accordingly, the transport mean number of scattering events $<n>$ is defined as follows where the maximum radius of the distal end portion 32 of the balloon catheter 3 from the center is R.

$$<n> = R/Z_\infty = \mu'_s R \quad (3)$$

As described above, the transport mean free path $Z_\infty$ and the equivalent scattering coefficient $\mu'_s$ are able to be changed by adjusting the refractive index, diameter, and concentration of the light scattering particles. Therefore, by changing these values, the transport mean number of scattering events $<n>$ in Equation (3) is able to be changed.

Figure 8:
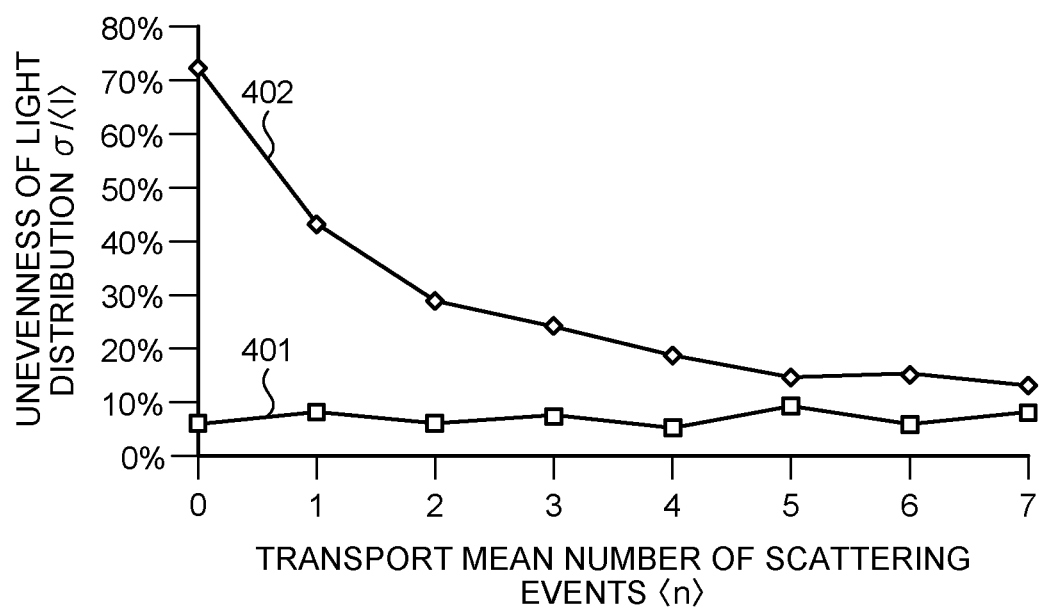
FIG. 8 is a diagram illustrating relations between transport mean number of scattering events and unevenness of light distributions.

FIG. 8 is a diagram illustrating a relation between transport mean number of scattering events $<n>$ and unevenness of light distribution $\sigma/<I>$. Herein, $\sigma$ is standard deviation of light intensity and $<I>$ is the mean value of light intensity. FIG. 8 illustrates the relation in a case where the distal end portion 32 is filled with 180 ml of an aqueous solution including light scattering particles and the maximum value of diameter of the distal end portion 32 is 70 mm (R=35 [mm]). A curve 401 representing the relation for the radial direction has a small variation in the unevenness of light distribution corresponding to the transport mean number of scattering events. This is due to the axial symmetry. In contrast, a curve 402 representing the relation for the azimuth direction decreases in the unevenness of light distribution as the transport mean number of scattering events increases, and when $<n> \geq 5$, the unevenness of light distribution reaches a level that is about the same as that for the radial direction.

In view of the above, it is understood that the relation, $\langle n \rangle \geq 5$, that is, the following relation, needs to be satisfied as a condition for the light distribution to be even in all directions.

$$\mu'_s \geq 5/R \quad (4)$$

If R illustrated in FIG. 6 equals 35 [mm], Expression (4) becomes Expression (5) below.

$$\mu'_s \geq 1/7 \ [\text{mm}^{-1}] \quad (5)$$

When the relations between the transport mean number of scattering events $\langle n \rangle$ and the unevenness of light distribution $\sigma/\langle n \rangle$ were found for cases where the maximum diameters of the distal end portion 32 were 105 mm (R=52.5 [mm]) and 140 mm (R=70 [mm]), similarly to the case where the maximum diameter was 70 mm, the unevenness of light distribution for the radial direction and the unevenness of light distribution for the azimuth direction were about the same when $\langle n \rangle \geq 5$. Therefore, in the range of sizes of bladders of human bodies, where the maximum diameters are about 70 mm to 140 mm, the condition of Expression (4) is valid. In general, as the maximum diameter of the distal end portion 32 increases, the number of scattering events for light emitted from the diffuser 22 increases and the brightness of the illumination becomes uniform. Therefore, even if the maximum diameter is larger than 70 mm, if at least the conditional expression (5) is satisfied, the transport mean number of scattering events becomes 5 or more and the brightness of the illumination becomes uniform.

In a case described below as a specific example of these numerical values, the liquid 101 is an aqueous solution including light scattering particles that are polyethylene particles having a diameter of 10 μm. In this case where polyethylene has a refractive index of 1.53, water has a refractive index of 1.33, and light emitted has a wavelength of 690 nm, the value of anisotropic parameter $\langle \cos \alpha \rangle$ becomes 0.91. In this case, if the transport mean number of scattering events $\langle n \rangle$ is 5, and the transport mean free path $Z_\infty$ is set at R/5=7 [mm] from Equation (3), the mean free path 1 becomes $Z_\infty(1-\langle \cos \alpha \rangle)=0.63$ [mm] from Equation (2). To achieve this mean free path, the concentration of particles in the aqueous solution is adjusted such that the number density of the polyethylene particles becomes 8760 particles/mm³. This concentration is achieved by adding 0.8 g of polyethylene particles having a diameter of 10 μm in 180 ml of water.

Figure 9:
FIG. 9 is a diagram illustrating how light beams are diffused, when the light beams are emitted by the diffuser and pass through liquid.

FIG. 9 is a diagram illustrating how light beams are diffused when the light beams are emitted by the diffuser 22 and pass through the liquid 101 including polyethylene as the light scattering particles, in the above setting. Light beams radially emitted from the diffuser 22 undergo multiple scattering due to the light scattering particles in the aqueous solution and travel zigzag, and thus advance thoroughly in all directions. When the total quantity of treatment light emitted to the spherical surface of the bladder was estimated by ray tracing simulation for light at a wavelength of 690 nm, 95.3% of light emitted by the diffuser 22 was found to reach the inner wall of the bladder. This corresponds to about twice the brightness for when light at the same wavelength is emitted by a conventional front-emitting light emitting unit.

Figure 10:
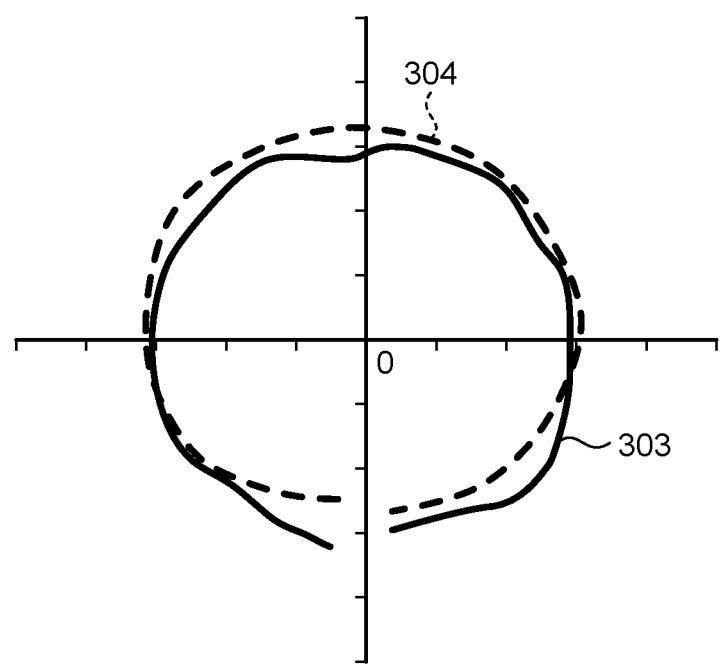
FIG. 10 is a diagram illustrating light distributions of light that is diffused as illustrated in FIG. 9.

FIG. 10 is a diagram illustrating light distributions of light for the radial direction and azimuth direction in this case, and similarly to FIG. 4, has a curve 303 and a curve 304 superimposed on each other, the curve 303 representing the distribution for the radial direction, the curve 304 representing the distribution for the azimuth direction. As evident from comparison with FIG. 4, in FIG. 10, not only the curve 303 representing the distribution for the radial direction, but also the curve 304 representing the distribution for the azimuth direction has an approximately isotropic light distribution. Therefore, the inner wall of a bladder is irradiated with light that is approximately uniform in brightness in all directions.

According to the description of the embodiment, the diffuser 22 has a porous structure having aggregated quartz beads in close contact with each other, but the diffuser 22 is not limited to this structure. For example, the diffuser 22 may have a cylindrical shape formed using a diffuser plate provided with multiple microlenses on a surface of a glass or plastic plate.

According to the embodiment described above, when a probe positioned in a distal end portion of a balloon catheter that has been spherically dilated emits light for treatment from a diffuser that is cylindrical, inside of the distal end portion has been filled with a liquid including light scattering particles, the liquid filling the inside of the distal end portion in a state where the distal end portion has been dilated, the liquid having an equivalent scattering coefficient $\mu'_s$ that satisfies a relation, $\mu'_s \geq 5/R$, where the maximum radius of the distal end portion dilated is R. As a result, even if a cylindrical diffuser is provided at a distal end of an optical fiber, light is able to be emitted uniformly in a spherical balloon, and unevenness of light distribution is able to be kept low.

Furthermore, according to the embodiment, if the equivalent scattering coefficient $\mu'_s$ of the liquid satisfies at least a condition, $\mu'_s \geq 1/7$ [mm$^{-1}$], for a case where the maximum radius R=35 [mm], unevenness of light distribution is able to be kept low regardless of sizes of bladders of human bodies.

Furthermore, according to the embodiment, as compared to a case where a conventional probe that illuminates forward only is used, the degree of light scattering by the scattering medium may be weak. Therefore, without having to increase the concentration of the light scattering particles in the liquid 101 more than necessary, the inner wall of a bladder is able to be illuminated with bright treatment light with the liquid 101 increased in transparency than conventionally done.

Modified Example

In this modified example, sedimentation of light scattering particles in liquid over time is considered. When a liquid including light scattering particles larger in specific gravity than water is used, the light scattering particles sediment and a supernatant is formed, over time. In the supernatant, multiple scattering of light does not occur, the transport mean number of scattering events is reduced, and the unevenness of light distribution is thus increased. In particular, when the thickness of the supernatant reaches the maximum radius R (see FIG. 6) of the distal end portion 32, multiple scattering does not occur at all and the transport mean number of scattering events becomes zero in the upper half of the distal end portion 32, and the light distribution thus becomes uneven for the azimuth direction. Therefore, at least while the probe 2 is emitting laser light, multiple scattering needs to continue being caused.

For the multiple scattering effect to be maintained in the liquid while laser light is being emitted for a time period t, floating velocity v of the light scattering particles, irradiation time period t, and the maximum radius R of the distal end portion 32 need to satisfy the following relation.

$$v \cdot t \leq R \quad (6)$$

In other words, the thickness of the supernatant generated while light is being emitted at least needs to be equal to or less than the maximum radius R of the distal end portion 32. For example, if the maximum radius R is 35 mm, and the irradiation time period t is 1 hour, from Expression (6) above, the following expression is obtained.

$$v \leq 9.7 \; [\mu m/sec] \quad (7)$$

According to Stokes' law, the floating velocity v of the light scattering particles in the liquid is expressed as follows, by using the diameter d of the particles, the viscosity coefficient of water $\eta$, the acceleration of gravity g, the density of the particles $\rho_S$, and the density of water $\rho_W$.

$$v = (\rho_S - \rho_W) g d^2 / 18 \eta \quad (8)$$

Figure 11:
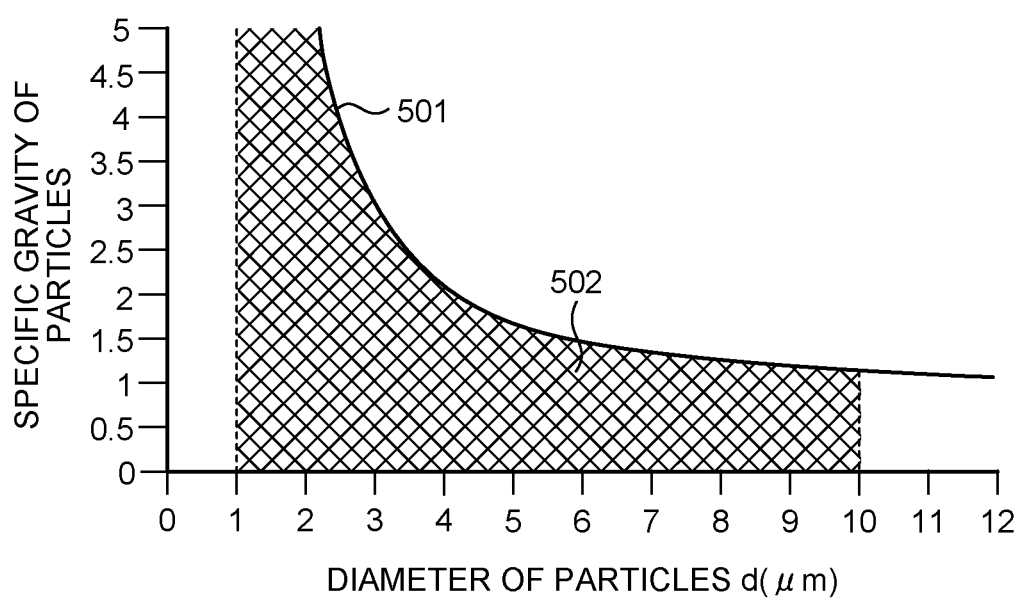
FIG. 11 is a diagram illustrating a relation between diameter and specific gravity of particles satisfying a condition for maintaining effects of multiple scattering of light in liquid.

FIG. 11 is a diagram illustrating a relation between the diameter d of the particles and the specific gravity ($\rho_S/\rho_W$) of the particles, satisfying the conditional expression (7). In FIG. 11, the horizontal axis represents the diameter d and the vertical axis represents the specific gravity. In FIG. 11, an area 502 between a curve 501 and the horizontal axis is an area satisfying the conditional expression (7).

Specific gravities of plastics typically used as the light scattering particles are 0.9 to 1.4. Specifically, for example, the specific gravity of polypropylene (PP) is 0.9 to 0.91, the specific gravity of polyethylene (PE) is 0.94 to 0.96, the specific gravity of polyethylene terephthalate (PET) is 1.34 to 1.39, the specific gravity of polymethyl methacrylate (PMMA) is 1.21 to 1.28, and the specific gravity of nylon/polyamide (NA) is 1.12 to 1.14. The particle diameter d satisfying the conditional expression (6) in this case is about 1 μm to 7 μm.

Specific gravities of inorganic materials typically used as the light scattering particles are 2.2 to 4.0. Specifically, for example, the specific gravity of silica ($SiO_2$) is 2.2, the specific gravity of titanium dioxide ($TiO_2$) is 4.0, and the specific gravity of calcium carbonate ($Ca_2O_3$) is 2.7. The particle diameter d satisfying the conditional expression (6) in this case is about 1 μm to 4 μm.

When the maximum radius R of the distal end portion 32 is larger than 35 mm, the time needed for sedimentation becomes longer, and thus light scattering particles having a diameter d similar to those mentioned above may be used.

When the light scattering particles are polyethylene particles, since the specific gravity of polyethylene is 0.94 to 0.96 and a little lower than that of water, the polyethylene particles float toward the surface while laser light is being emitted. Therefore, as particles near the bottom of the distal end portion 32 float toward the surface, a transparent region is formed. The floating velocity v of polyethylene particles becomes very slow at $v = 1.6087 \; [\mu m/sec]$ when specific numerical values, $d = 10 \times 10^{-6} \; [m]$, $\eta = 101.6 \times 10^{-5} \; [Pa \cdot s]$, $g = 9.80665 \; [m/s^2]$, $\rho_S = 0.97 \times 10^3 \; [kg/m^3]$, and $\rho_W = 1 \times 10^3 \; [kg/m^3]$, are substituted into Equation (8). For example, if the light irradiation time period t is 1 hour, the polyethylene particles float during that light irradiation time period t by a distance of about 5.8 mm. In this case, a transparent region having a thickness of about 5.8 mm is formed at the bottom of the distal end portion 32 having the maximum diameter of 70 mm (R=35 [mm]) but the light scattering property of the liquid 101 filling a region around the probe 2 is not lost.

As illustrated in FIG. 8, by the formation of the transparent region at the bottom of the distal end portion 32 of the balloon catheter 3, the transport mean numbers of scattering events of the light beams emitted downward are reduced from 5 to 4, but the unevenness of light distribution in that case is about 20% at most. Therefore, this level of variation in light intensity would not influence the effectiveness of treatment.

According to the modified example described above, by setting the diameter of the light scattering particles at a value that satisfies the conditional expression (6) correspondingly to the specific gravity of the light scattering particles, even if the light scattering particles sediment or float in the liquid, the inner wall of a bladder is able to be irradiated with laser light evenly and unevenness of light distribution is able to be kept low while the inner wall of the bladder is being irradiated with the laser light.

According to the disclosure, light is able to be emitted evenly in a spherical balloon and unevenness of light distribution is able to be kept low, even if a cylindrical diffuser is provided at a distal end of an optical fiber.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light treatment system, comprising:
    a light source configured to generate light having a wavelength of 690 nm;
    a probe including an optical fiber configured to propagate the light from the light source, and a diffuser having a cylindrical shape and provided at a distal end of the optical fiber, the diffuser being configured to diffuse the light from a surface of the cylindrical shape;
    a balloon catheter into which the probe is inserted, the balloon catheter being configured to be inserted into the bladder, the balloon catheter including a distal end portion configured to be spherically dilated in the bladder; and
    a liquid that includes light scattering particles and fills an inside of the distal end portion when the distal end portion is dilated, the liquid having a scattering coefficient $\mu'_s$ equal to or larger than 5/R, where R is a maximum radius of the distal end portion when dilated;
    wherein the maximum radius of the distal end portion is between 35 mm and 70 mm, inclusive of 35 mm and 70 mm;
    a diameter of the light scattering particles is within a range of 1 μm to 4 μm, inclusive of 1 μm and 4 μm; and
    a specific gravity of the light scattering particles is within a range of 0.9 to 1.4 inclusive of 0.9 and 1.4.

2. The light treatment system according to claim 1, wherein the scattering coefficient $\mu'_s$ is 1/7 [mm].

3. The light treatment system according to claim 2, wherein the light scattering particles are made of a plastic selected from a group consisting of polypropylene, polyethylene, polyethylene terephthalate, polymethyl methacrylate, and nylon.

4. The light treatment system according to claim 2, wherein the light scattering particles are made of an inorganic material selected from a group of silica, titanium dioxide, and calcium carbonate.

5. The light treatment system according to claim 1, wherein the light scattering particles are made of a plastic selected from a group consisting of polypropylene, polyethylene, polyethylene terephthalate, polymethyl methacrylate, and nylon.

6. The light treatment system according to claim 1, wherein the light scattering particles are made of an inorganic material selected from a group consisting of silica, titanium dioxide, and calcium carbonate.

* * * * *